United States Patent [19]

Hubschwerlen et al.

[11] Patent Number: 5,283,248
[45] Date of Patent: Feb. 1, 1994

[54] AMINO SUBSTITUTED PYRIMIDO[1,6-2]BENZIMIDAZOLES

[75] Inventors: Christian Hubschwerlen, Durmenach, France; Ivan Kompis, Oberwil, Switzerland; Jean-Luc Specklin, Kembs-Loechle, France

[73] Assignee: Hoffmann-La Roche Inc., Nutley, N.J.

[21] Appl. No.: 904,245

[22] Filed: Jun. 25, 1992

Related U.S. Application Data

[63] Continuation-in-part of Ser. No. 708,642, May 31, 1991, abandoned, which is a continuation-in-part of Ser. No. 612,333, Nov. 13, 1990, abandoned.

[30] Foreign Application Priority Data

Nov. 21, 1989 [CH] Switzerland ............ 4165/89
Aug. 17, 1990 [CH] Switzerland ............ 2688/90
Aug. 30, 1990 [CH] Switzerland ............ 2817/90

[51] Int. Cl.$^5$ ............ A61K 31/505; C07D 487/04; C07D 235/16; C07C 275/40
[52] U.S. Cl. ............ 514/267; 514/212; 514/218; 514/228.5; 514/233.2; 540/575; 540/600; 544/60; 544/115; 544/250; 544/370; 544/391; 544/392; 544/393; 546/271; 546/337; 548/306.1; 548/309.7; 548/310.1; 564/34; 564/35; 564/50; 564/218; 564/431
[58] Field of Search ............ 544/250, 60, 115; 540/575, 600; 514/212, 267, 218, 228.5, 233.2

[56] References Cited

U.S. PATENT DOCUMENTS

4,209,523  6/1980  Lafon ............ 514/394
4,246,196  1/1981  Arndt et al. ............ 564/50

FOREIGN PATENT DOCUMENTS

0012983  7/1980  European Pat. Off. .
2930333  2/1981  Fed. Rep. of Germany .

OTHER PUBLICATIONS

Hubschwerlen et al., *Chemical Abstracts*, vol. 116, No. 6577 (1992) (Abstract for CA 2028530, May 22, 1991).
Yogo et al Chem. Pharm. Bull. 32(9) pp. 3695-3697 (1984).
Badawey et al J. Heterocyclic Chem. 26 pp. 1401-1404 Sep. Oct. 1989.
Badawey et al. J. Heterocyclic Chem. 26 pp. 405-408 (1989).
R. Otter and N. R. Cozzarelli, Methods in Enzymology, vol. 100, pp. 171-180 (1983).
Davies et al. Pyrimido (3,4-a)Benzimidazole Novel Ring System, Journal of the Chemical Society, pp. 5125-5127 (1965).

*Primary Examiner*—Emily Bernhardt
*Attorney, Agent, or Firm*—George M. Gould; George W. Johnston; Ellen Ciambrone Coletti

[57] ABSTRACT

The present invention relates to novel substituted pyrimidobenzimidazole derivatives of the formula

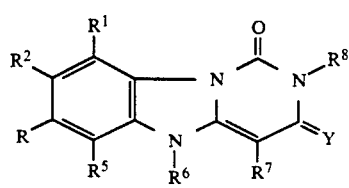

wherein the substituents are as described in the specification, and pharmaceutically acceptable salts thereof.

The products have an inhibitory action on the DNA-gyrase activity in bacteria. They can accordingly be used for the prevention or control of bacterial infections.

70 Claims, No Drawings

AMINO SUBSTITUTED PYRIMIDO[1,6-2]BENZIMIDAZOLES

RELATED APPLICATIONS

This application is a continuation-in-part of U.S. application Ser. No. 07/708,642, filed May 31, 1991, now abandoned which is a continuation-in-part of U.S. application Ser. No. 07/612,333, filed Nov. 13, 1990, now abandoned.

BRIEF SUMMARY OF THE INVENTION

The present invention relates to novel substituted pyrimidobenzimidazole derivatives of the formula

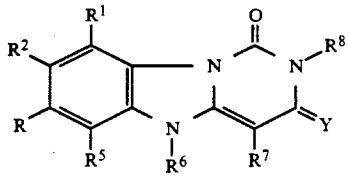

wherein
$R^1$ is hydrogen, halogen or amino,
$R^2$ is halogen,
R is a lower alkyl-substituted 4-pyridyl group or a group $R^3R^4N$— in which $R^3$ and $R^4$ each are hydrogen or lower alkyl or together signify a group of the formula —$(CH_2)_n$—X—$(CH_2)_m$— or —$(CH_2)_p$— which is unsubstituted or substituted by lower alkyl, amino, lower aminoalkyl, mono- or di(lower alkyl)amino-lower alkyl, oxo or the group —$COOR^a$ or —$CONR'R''$,
n and m each are the number 1, 2 or 3, with the proviso that n+m is a maximum of 5,
p is the number 4, 5 or 6,
X is an oxygen or sulfur atom or the group —NR'''—,
$R^a$ is hydrogen, lower alkyl, lower alkenyl, phenyl or phenyl which is mono-, di- or trisubstituted by halogen, lower alkyl or hydroxy,
R' and R'' each are hydrogen or lower alkyl,
R''' is hydrogen, hydroxy, lower alkyl or lower aminoalkanoyl,
$R^5$ is hydrogen, halogen, lower alkoxy or amino,
$R^6$ is lower alkyl, lower cycloalkyl, lower haloalkyl, phenyl or phenyl which is mono-, di- or trisubstituted by halogen, lower alkyl, hydroxy or lower alkoxy,
$R^7$ is hydrogen, lower alkyl or carboxy,
$R^8$ is hydrogen, hydroxy, lower alkoxy, amino, lower alkylamino or di-lower alkylamino and
Y is an oxygen or sulfur atom,
and pharmaceutically acceptable salts thereof.

The novel compounds of formula I above have valuable pharmacological properties. They display an inhibitory action on the DNA-gyrase activity in bacteria and can accordingly be used for the control or prevention of bacterial infections.

DETAILED DESCRIPTION OF THE INVENTION

The present invention relates to novel substituted pyrimidobenzimidazole derivatives of the formula

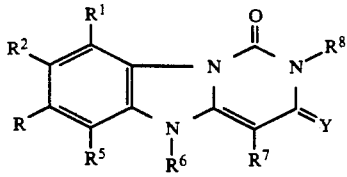

wherein
$R^1$ is hydrogen, halogen or amino,
$R^2$ is halogen,
R is a lower alkyl-substituted 4-pyridyl group or a group $R^3R^4N$— in which $R^3$ and $R^4$ each are hydrogen or lower alkyl or together signify a group of the formula —$(CH_2)_n$—X—$(CH_2)_m$— or —$(CH_2)_p$— which is unsubstituted or substituted by lower alkyl, amino, lower aminoalkyl, mono- or di(lower alkyl)amino-lower alkyl, oxo or the group —$COOR^a$ or —$CONR'R''$,
n and m each are the number 1, 2 or 3, with the proviso that n+m is a maximum of 5,
p is the number 4, 5 or 6,
X is an oxygen or sulfur atom or the group —NR'''—,
$R^a$ is hydrogen, lower alkyl, lower alkenyl, phenyl or phenyl which is mono-, di- or trisubstituted by halogen, lower alkyl or hydroxy,
R' and R'' each are hydrogen or lower alkyl,
R''' is hydrogen, hydroxy, lower alkyl or lower aminoalkanoyl,
$R^5$ is hydrogen, halogen, lower alkoxy or amino,
$R^6$ is lower alkyl, lower cycloalkyl, lower haloalkyl, phenyl or phenyl which is mono-, di- or trisubstituted by halogen, lower alkyl, hydroxy or lower alkoxy,
$R^7$ is hydrogen, lower alkyl or carboxy,
$R^8$ is hydrogen, hydroxy, lower alkoxy, amino, lower alkylamino or di-lower alkylamino and
Y is an oxygen or sulfur atom,
and pharmaceutically acceptable salts thereof.

The novel compounds of formula I above have valuable pharmacological properties. They display an inhibitory action on the DNA-gyrase activity in bacteria and can accordingly be used for the control or prevention of bacterial infections.

Objects of the present invention are: the above compounds of formula I and their use as therapeutically active substances; a process and intermediates for their preparation, medicaments based on these novel substances; as well as the use of the novel compounds of formula I for the control or prevention of bacterial infections and for the preparation of antibacterially-active medicaments.

The term "lower" used in the scope of the present description denotes residues and compounds having a maximum of 7, preferably a maximum of 4, carbon atoms. The term "alkyl", taken alone or in combinations such as "alkyl group", denotes straight-chain or branched saturated hydrocarbon residues such as methyl, ethyl, n-propyl, i-propyl, n-butyl, s-butyl, i-butyl, t-butyl, and the like. The term "alkenyl" denotes straight-chain or branched hydrocarbon residues which contain at least one olefinic double bond, such as allyl, 2-butenyl and the like. The term "cycloalkyl" denotes cyclic saturated hydrocarbon residues such as cyclopropyl and the like. The term "alkanoyl" denotes residues of straight-chain or branched saturated fatty acids, such as acetyl and the like. The term "halogen" denotes the four forms fluorine, chlorine, bromine and iodine. The term "alkoxy" denotes alkyl groups attached via an oxygen atom, such as methoxy, ethoxy and the like.

Preferably, $R^1$ and $R^5$ each are hydrogen. $R^2$ is preferably fluorine. $R^3$ and $R^4$ preferably together are a group of the formula —$(CH_2)_n$—X—$(CH_2)_m$— or a group of the formula —$(CH_2)_p$— which is substituted by the group —$COOR^a$, wherein n and m each are the number 2, p is the number 4, X is the group —$NR'''$—, $R^a$ is lower alkyl and $R'''$ is hydrogen, lower alkyl or lower aminoalkanoyl. $R^3R^4N$— is preferably 1-piperazinyl or 4-methyl-1-piperazinyl. $R^6$ is preferably lower alkyl, especially ethyl, or lower cycloalkyl, especially cyclopropyl. $R^7$ is preferably hydrogen or carboxy. $R^8$ is preferably hydrogen, hydroxy, amino, methylamino or dimethylamino. Y is preferably an oxygen atom. When R is a lower alkyl-substituted 4-pyridyl group, it is preferably the 3,5-dimethyl-4-pyridyl group.

The compounds listed hereinafter are representative members of the novel class of substance defined by formula I:

5-Ethyl-8-fluoro-7-(4-methyl-1-piperazinyl)-pyrimido[1,6-a]benzimidazole-1,3(2H,5H)-dione, 5-cyclopropyl-8-fluoro-7-(1-piperazinyl)-pyrimido[1,6-a]benzimidazole-1,3(2H,5H)-dione, 5-ethyl-9-fluoro-3,5-dihydro-8-(4-methyl-1-piperazinyl)-3-thioxopyrimido[1,6-a]benzimidazol-1(2H)-one, 5-cyclopropyl-8-fluoro-2-hydroxy-7-(1-piperazinyl)-pyrimido[1,6-a]benzimidazole-1,3(2H,5H)-dione, tert-butyl rac-1-[5-cyclopropyl-8-fluoro-2,3-dihydro-1,3-dioxopyrimido[1,6-a]benzimidazole-5(1H)-yl]-2-pyrrolidinecarboxylate, 7-(4-L-alanyl-1-piperazinyl)-5-cyclopropyl-8-fluoro-2-hydroxypyrimido[1,6-a]benzimidazole-1,3(2H,5H)-dione, 1-[5-cyclopropyl-8-fluoro-1,2,3,5-tetrahydro-2-hydroxy-1,3-dioxopyrimido[1,6-a]benzimidazol-7-yl]-L-proline tert-butyl ester, 5-ethyl-8-fluoro-7-(1-piperazinyl)pyrimido[1,6-a]benzimidazole-1,3(2H,5H)-dione, 5-ethyl-8-fluoro-2-hydroxy-7-(4-methyl-1-piperazinyl)-pyrimido[1,6-a]benzimidazole-1,3(2H,5H)-dione, 5-cyclopropyl-8-fluoro-1,2,3,4-tetrahydro-1,3-dioxo-7-(1-piperazinyl)pyrimido[1,6-a]benzimidazole-4-carboxylic acid, 5-ethyl-8-fluoro-2-hydroxy-7-(1-piperazinyl)-pyrimido[1,6-a]benzimidazole-1,3(2H,5H)-dione, 2-amino-5-cyclopropyl-8-fluoro-7-(1-piperazinyl)-pyrimido[1,6-a]benzimidazole-1,3(2H,5H)-dione, 5-cyclopropyl-8-fluoro-2-(methylamino)-7-(1-piperazinyl)pyrimido[1,6-a]benzimidazole-1,3-(2H,5H)-dione and 5-cyclopropyl-2-(dimethylamino)-8-fluoro-7-(1-piperazinyl)pyrimido[1,6-a]benzimidazole-1,3(2H,5H)-dione, 5-cyclopropyl-8-fluoro-2-hydroxy-7-(4-methyl)-1-piperazinyl)-1H-pyrimido[1,6-a]benzimidazole-1,3-(2H,5H)-dione.

The novel compounds of formula I and their pharmaceutically acceptable salts can be prepared in accordance with the invention by a) reacting a compound of the formula

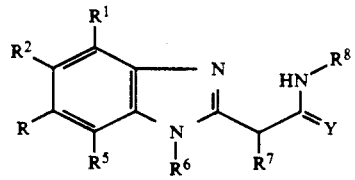

wherein R, Y, $R^1$, $R^2$, $R^5$, $R^6$, $R^7$ and $R^8$ are as described above, with the proviso that free hydroxy, amino and carboxy groups which may be present are in protected form, optionally in the presence of a base with a compound of the formula

X—CO—X    III wherein X is a leaving group, or b) reacting a compound of the formula

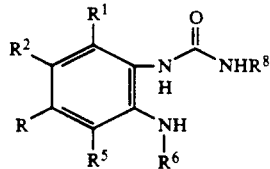

wherein R, $R^1$, $R^2$, $R^5$, $R^6$ and $R^8$ are as described above with the proviso that free hydroxy, amino and carboxy groups which may be present are in protected form, in the presence of a base with a compound of the formula

RaOOC—CHR$^7$—COORa    V wherein Ra is lower alkyl and $R^7$ is as described above, with the proviso that a free carboxy group which may be present is in protected form, or c) reacting a compound of the formula

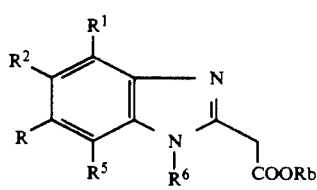

wherein Rb is a carboxy protecting group and R, $R^1$, $R^2$, $R^5$ and $R^6$ are as described above with the proviso that free hydroxy, amino and carboxy groups which may be present are in protected form, with 2 molar equivalents of chloroacetyl isocyanate, whereupon any protecting groups present are cleaved off and a compound of formula I obtained is, if desired, converted into a pharmaceutically acceptable salt.

In the above processes the reactive free hydroxy, amino and carboxy groups which may be present in the starting materials must be blocked by protecting groups. These instances and the choice of the respective suitable protecting groups will be readily recognisable by a person skilled in the art. There come into consideration for the present purpose especially the protecting groups which are usually used in peptide chemistry.

An especially suitable amino protecting group is the t-butoxycarbonyl group which can be cleaved off readily, for example, by treatment with trifluoroacetic acid, dilute HCl/dioxane or sodium iodide/trimethylchlorosilane/acetonitrile.

An especially suitable hydroxy protecting group is the benzyl group which can be cleaved off readily, for example, by reduction with elementary hydrogen on a suitable catalyst (for example, palladium/carbon). Suitable solvents for this are, for example, lower alcohols such as ethanol and dimethylformamide.

An especially suitable carboxy protecting group is the p-nitrobenzyl group which also can be cleaved off by reduction with elementary hydrogen in the presence of a suitable catalyst (for example, palladium/carbon). Suitable solvents for this are also lower alcohols such as ethanol and dimethylformamide.

In accordance with process variant a) the compounds of formula I can be prepared by reacting a compound of formula II with a compound of formula III optionally in the presence of a base. As the compound of formula III there is preferably used phosgene or a precursor thereof or N,N'-carbonyldiimidazole, with the last-named compound being particularly preferred. A tertiary amine such as triethylamine or a bicyclic amidine such as 1,8-diazabicyclo[5.4.0]undec-7-ene (DBU) or 1,5-diazabicyclo[4.3.0]non-5-ene (DBN) is preferably used as the base. Suitable solvents are, for example, open-chain and cyclic ethers such as diethyl ether, t-butyl methyl ether and tetrahydrofuran (THF). The reaction is preferably carried out in a temperature range of about room temperature to about 100° C.

In accordance with process variant b) the compounds of formula I can be prepared by reacting a compound of formula IV with a compound of formula V in the presence of a base. A lower alkali metal alcoholate such as sodium methanolate or potassium methanolate is preferably used as the base. The corresponding lower alcohol, for example, methanol, is preferably used as the solvent. This reaction is preferably carried out at room temperature.

Compounds of formula I in which $R^7$ is carboxy, $R^8$ is hydrogen and Y is an oxygen atom can be prepared in accordance with process variant c). The reaction of a compound of formula VI with 2 molar equivalents of chloroacetyl isocyanate is preferably carried out in an inert organic solvent, with for example, open-chain and cyclic ethers such as diethyl ether, t-butyl methyl ether and tetrahydrofuran coming into consideration for this purpose. The reaction is preferably carried out in a temperature range of from about 0° C. to about room temperature.

Pharmaceutically acceptable salts of compounds of formula I can be prepared according to known methods. Compounds of formula I which have a free carboxy group can be converted into such salts, for example, by treatment with a suitable base. Alkali metal salts such as the sodium and potassium salts are examples of such salts.

Compounds of formula I which have a basic amino group can be converted into acid addition salts, for example, by treatment with pharmaceutically acceptable acids. As acid addition salts there come into consideration not only salts with inorganic acids but also salts with organic acids, for example, hydrochlorides, hydrobromides, sulfates, nitrates, citrates, tartrates, acetates, maleates, succinates, methanesulphonates, p-toluenesulfonates and the like.

The compounds of formulae II, IV and VI which are used as starting materials are novel and are also objects of the present invention. These starting materials can be prepared according to known methods. The Examples which follow below contain detailed information concerning the preparation of these starting materials.

The intermediates corresponding to formula I in which free hydroxy, amino and/or carboxy groups present are in protected form, which are obtainable according to process variants a), b) and c), are also objects of the invention.

As mentioned earlier, the compounds of formula I in accordance with the invention and their pharmaceutically acceptable salts display an inhibitory action on the DNA-gyrase activity in bacteria. They can accordingly be used for the prevention or control of bacterial infections.

The inhibitory action on the DNA-gyrase activity in bacteria can be determined, for example, by means of the supercoiling method described by R. Otter and N. R. Cozzarelli in Methods in Enzymology, Vol. 100, pp. 171–180 (1983). The DNA-gyrase used was isolated from E. coli N4186 and from the sub-unit B of E. coli MK47 (Mitsuchi et al., JBL 159, 9199–9201 (1984)). Relaxed pUC18 or pUC19 plasmid DNA was used as the substrate. The results determined in this test are compiled in the following Table, with the results being expressed as the MNC (maximum non-effective concentration) in μg/ml.

TABLE

| Product from | Activity MNC in μg/ml | Toxicity $LD_{50}$ in mg/kg |
|---|---|---|
| Example 1 | 2 | — |
| Example 2 | 0.45 | 30 (i.v.) >2000 (p.o.) |
| Example 3 | 2 | — |
| Example 4 | 2 | 30 (i.v.) >4000 (p.o.) |
| Example 8 | 1 | — |

The compounds of formula I and their pharmaceutically acceptable salts can be used as medicaments in mammals, for example, in the form of pharmaceutical preparations for enteral or parenteral application. They can be administered, for example; perorally, for example in the form of tablets, coated tablets, dragees, hard and soft gelatin capsules, solutions, emulsions or suspensions; rectally, for example, in the form of suppositories; or parenterally, for example, in the form of injection solutions.

The pharmaceutical preparations can be prepared in a manner which is familiar to any person skilled in the art by bringing the products in accordance with the invention, optionally in combination with other therapeutically valuable substances, into a galenical administration form together with suitable, non-toxic, inert, therapeutically compatible solid or liquid carrier materials and, if desired, the usual pharmaceutical adjuvants.

Suitable carrier materials are not only inorganic carrier materials, but also organic carrier materials. Thus, lactose, maize starch or derivatives thereof, talc, stearic acid or its salts can be used, for example, as carrier materials for tablets, coated tablets, dragees and hard gelatin capsules. Suitable carrier materials for soft gelatin capsules are, for example, vegetable oils, waxes, fats and semi-solid and liquid polyols (depending on the nature of the active ingredient no carriers are, however, required in the case of soft gelatin capsules). Suitable carrier materials for the preparation of solutions and syrups are, for example, water, polyols, saccharose, invert sugar and glucose. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols.

As pharmaceutical adjuvants there come into consideration the usual stabilizing, preserving, wetting and emulsifying agents, flavor-improving agents, salts for varying the osmotic pressure, buffer substances, solubilizers, coloring and coating agents and antioxidants.

The dosage of the compounds of formula I can vary within wide limits depending on the bacterial infection to be controlled, the age and the individual condition of the mammal or host to be treated and on the mode of administration and will, of course, be fitted to the individual requirements in each particular case. A daily dosage of from about 0.05 g to about 4 g, especially from about 0.1 g to about 2 g, can be conveniently utilized. Depending on the dosage it is convenient to administer the daily dosage in several unit dosages.

The pharmaceutical preparations conveniently contain from about 25 to about 2000 mg, preferably from about 50 to about 1000 mg, of a product in accordance with the invention.

The following Examples serve to illustrate the present invention in more detail. However, they are not intended to limit its scope in any manner. All temperatures are given in degrees Celsius.

EXAMPLE 1 a) A suspension of lithium aluminium hydride (44.1 g, 1.16 mmol) in absolute ether (700 ml) is treated dropwise with a solution of 3'-chloro-4'-fluoroacetanilide (BE Patent No. 891537; 109 g, 0.576 mol) in absolute THF (350 ml). The suspension obtained is stirred for 2 hours, then cooled to 0° and treated with a Rochelle salt solution (350 ml). The crystals obtained are filtered off and washed with ether. The organic solution is dried over magnesium sulphate and the solvent is distilled off under reduced pressure. There are obtained 97.5 g (97.5%) of 3-chloro-N-ethyl-4-fluoroaniline as an amorphous material.

b) A solution of 3-chloro-N-ethyl-4-fluoroaniline (97.4 g, 0.56 mmol) in glacial acetic acid (225 ml) is treated at 5° with acetic anhydride (105 ml, 1.12 mol). The solution is stirred for one hour, then poured on to ice/water (250 ml) and extracted with ethyl acetate (2×200 ml). The combined phases are washed in succession with water (100 ml), 2N sodium hydroxide solution (100 ml), saturated sodium bicarbonate solution (100 ml), water (10 ml) and 10 percent sodium chloride solution (100 ml). The solution is dried over magnesium sulfate and evaporated. The residue is recrystallized from n-hexane. There are obtained 102 g (84.2%) of 3'-chloro-N-ethyl-4'-fluoroacetanilide.

Microanalysis $C_{10}H_{11}ClFNO$: Calc.: C 55.70, H 5.14, N 6.50. Found: C 55.04, H 5.43, N 6.57.

c) 3'-Chloro-N-ethyl-4'-fluoroacetanilide (101 g, 0.468 mmol) is dissolved in conc. sulfuric acid (300 ml). A solution of potassium nitrate (57 g, 0.564 mol) in conc. sulfuric acid (220 ml) is added dropwise thereto at 5°. The solution obtained is stirred overnight, then poured on to ice/water and extracted with ethyl acetate (2×200 ml). The organic phase is washed in succession with water (200 ml), saturated sodium bicarbonate solution (100 ml) and saturated sodium chloride solution (100 ml). The organic phase is treated with active charcoal, filtered and dried over magnesium sulfate. The solvent is distilled off and the residue is recrystallized from ether/n-hexane. There are obtained 74.8 g (61%) of 5'-chloro-N-ethyl-4'-fluoro-2'-nitroacetanilide with a m.p. of 68°.

Microanalysis $C_{10}H_{10}FClN_2O_3$: Calc.: C 46.08, H 3.87, N 10.75. Found: C 45.99, H 3.92, N 10.82.

d) 5'-Chloro-N-ethyl-4'-fluoro-2'-nitroacetanilide (74 g, 0.284 mmol) is treated with N-methylpiperazine (126 ml, 1.13 mol) and the solution obtained is stirred at 60° for 2 hours. The reaction mixture is evaporated, the residue is dissolved in ethyl acetate (250 ml) and washed in succession with water (3×100 ml) and 10 percent sodium chloride solution (100 ml). The organic solution is dried over magnesium sulfate and evaporated. The residue is recrystallized from ethyl acetate/n-hexane. There are obtained 72.3 g (78.5%) of N-ethyl-4'-fluoro-5'-(4-methyl-1-piperazinyl)-2'-nitroacetanilide with a m.p. of 117°-119°.

Microanalysis $C_{15}H_{21}FN_4O_3$: Calc.: C 55.50, H 6.53, N 17.27. Found: C 55.47, H 6.73, N 17.14.

e) A solution of N-ethyl-4'-fluoro-5'-(4-methyl-1-piperazinyl)-2'-nitroacetanilide (20 g, 61 mmol) in methanol (160 ml) is treated with an aqueous potassium hydroxide solution (34.6 g, 616 mmol). The solution is heated to 80° for 3 hours and thereafter cooled to room temperature. The crystals obtained are filtered off and washed with water. There are obtained 13.7 g (78.7%) of 1-(5-(ethylamino)-2-fluoro-4-nitrophenyl)-4-methylpiperazine with a m.p. of 149°-150°.

Microanalysis $C_{13}H_{19}FN_4O_2$: Calc.: C 55.31, H 6.78, N 19.85. Found: C 55.16, H 6.95, N 19.81.

f) A solution of 1-(5-(ethylamino)-2-fluoro-4-nitrophenyl)-4-methylpiperazine (10 g) in THF (200 ml) is hydrogenated over 5 percent palladium/carbon (Pd/C) under hydrogen. At the end of the reduction the catalyst is filtered off, the filtrate is treated directly with a solution of sodium cyanate (230 mg) in water (50 ml) and the pH is adjusted to 3.5 with conc. HCl (2.5 ml). After stirring under argon for two hours the pH is adjusted to 8 with 4N NaOH and the solution is evaporated under reduced pressure. The residue is extracted with methanol/ethyl acetate (1:4). The solution is filtered, decolorized with active charcoal and evaporated in a vacuum. The residue is taken up in warm ethyl acetate. After cooling the crystals are filtered off and dried. There is obtained 0.63 g (60%) of 1-[2-(N-ethylamino)-5-fluoro-4-(4-methyl-1-piperazinyl]phenyl-urea.

Microanalysis $C_{14}H_{22}FN_5O$: Calc.: C 56.93, H 7.51, N 23.71. Found: C 57.16, H 7.64, N 23.80.

g) A solution of 1-[2-(N-ethylamino)-5-fluoro-4-(4-methyl-1-piperazinyl]phenyl-urea (640 mg) in methanol is treated with a freshly prepared methanolic solution of sodium methylate (from 150 mg of sodium) and heated under reflux for a short time. After cooling the solution is treated with diethyl malonate and stirred for 6 hours. The solution obtained is poured into a mixture of ice and 2N HCl (50 ml). The methanol is evaporated and the aqueous phase is extracted with ethyl acetate (3×100 ml) and methylene chloride (2×100 ml). After drying over magnesium sulfate the solvent mixture is evaporated and the residue is suspended in a small amount of cold ethyl acetate and filtered off. There are obtained 130 mg (17%) of 5-ethyl-8-fluoro-7-(4-methyl-1-piperazinyl)pyrimido[1,6-a]benzimidazole-1,3(2H,5H)-dione.

MS: 345(M) Microanalysis (hydrochloride)

$C_{17}H_{21}ClFN_5O_2$: Calc.: C 53.47, H 5.54, N 18.34. Found: C 52.97, H 5.52, N 18.12.

EXAMPLE 2 a) 1-Chloro-2,5-difluoro-4-nitrobenzene (3.69 g, 19 mmol) is treated at 0° with diethylamine (2.3 g, 23 mmol) and cyclopropylamine (1.3 g, 23 mmol). After 1 hour at 0° the suspension obtained is stirred at 25° for 16 hours. The reaction mixture is taken up in water (150 ml) and extracted with ethyl acetate. The organic phase is washed with 10 percent sodium chloride solution and dried over magnesium sulfate. After distillation of the solvent the residue is recrystallized from ethanol (50 ml). There are obtained 3.5 g (79%) of 5-chloro-N-cyclopropyl-4-fluoro-2-nitroaniline with a m.p. of 73.5°–75.5°.

Microanalysis $C_9H_8ClFN_2O_2$: Calc.: C 46.87, H 3.50, N 12.15. Found: C 46.59, H 3.64, N 12.15.

b) 5-Chloro-N-cyclopropyl-4-fluoro-2-nitroaniline (3.5 g, 15.2 mmol) is heated with N-acetylpiperazine (3.89 g, 30.4 mmol) and triethylamine (2.3 g 22.8 mmol) while stirring vigorously and held at 60° for 12 hours. The mass obtained is dissolved in water (200 ml) and extracted with ethyl acetate. The organic phase is washed with 10 percent sodium chloride solution and then dried over magnesium sulfate. After distillation of the solvent the residue is recrystallized from ethanol. There are obtained 4.57 g (93%) of 1-acetyl-4-[5-(cyclopropylamino)-2-fluoro-4-nitrophenyl]piperazine with a m.p. of 142°–143°.

Microanalysis $C_{15}H_{19}FN_4O_3$: Calc.: C 55.89, H 5.94, N 17.38. Found: C 55.66, H 5.94, N 17.35.

c) 1-Acetyl-4-[5-(cyclopropylamino)-2-fluoro-4-nitrophenyl]piperazine (17 g, 53 mmol) is dissolved in methanol (250 ml), treated with potassium hydroxide (29.6 g, 527 mmol) and heated under reflux for 3 hours. After distillation of the methanol, the residue is dissolved in ethyl acetate and the organic phase is washed in succession with water and sodium chloride solution and dried over magnesium sulfate. After distillation of the solvent the residue is dissolved in dioxane (100 ml) and treated with di-tert-butyl dicarbonate (13.8 g, 63.24 mmol) and an aqueous solution of sodium hydrogen carbonate (6.6 g, 79 mmol, in 60 ml of water). After stirring for 20 hours the suspension obtained is diluted with water. The crystals are filtered off, washed with water and recrystallized from ethanol. There are obtained 18.2 g (91%) of tert-butyl 4-[5-(cyclopropylamino)-2-fluoro-4-nitrophenyl]-1-piperazinecarboxylate with a m.p. of 159°–160°.

Microanalysis $C_{18}H_{25}FN_4O_4$: Calc.: C 56.83, H 6.62, N 14.73. Found: C 56.92, H 6.70, N 14.89.

d) tert-Butyl 4-[5-(cyclopropylamino)-2-fluoro-4-nitrophenyl]-1-piperazinecarboxylate (17.21 g, 45.2 mmol) is dissolved in methanol (500 ml) and hydrogenated with 5 percent Pd/C (500 mg) under hydrogen at normal pressure. The hydrogen uptake amounts to 3.04 l. The palladium/carbon is filtered off under an inert gas and the methanol is distilled off under reduced pressure. The residue is dried in a high vacuum, then dissolved in DMF (150 ml) and treated with ethyl 3-ethoxy-3-iminopropanoate hydrochloride (17.3 g, 88.4 mmol). The solution obtained is heated to 50° for 2 hours. The DMF is distilled off, the residue is dissolved in water and the pH is adjusted to 8.0 with saturated sodium bicarbonate solution. The solution is extracted with ethyl acetate and the organic phase is washed in succession with water, 10 percent sodium chloride solution and then dried over magnesium sulfate. The solution is evaporated under reduced pressure and the residue is chromatographed on silica gel (eluent:ethyl acetate). The product is then recrystallized from ethyl acetate/hexane. There are obtained 15.5 g (78%) of ethyl 6-[4-(tert-butoxycarbonyl)-1-piperazinyl]-1-cyclopropyl-5-fluoro-2-benzimidazoleacetate with a m.p. of 152°–153°.

Microanalysis $C_{23}H_{31}FN_4O_4$: Calc.: 61.87, H 7.00, N 12.55. Found: C 62.13, H 7.17, N 12.68.

e) Ethyl 6-[4-(tert-butoxycarbonyl)-1-piperazinyl]-1-cyclopropyl-5-fluoro-2-benzimidazoleacetate (4.5 g, 10 mmol) is dissolved in ethanol (100 ml) and treated with ammonium chloride (5.35 g, 100 mmol) and 25 percent ammonium hydroxide solution (50 ml). The suspension obtained is stirred at 50° for 18 hours and thereafter evaporated under reduced pressure. The residue is suspended in ethyl acetate (150 ml) and the insoluble ammonium chloride is filtered off. The filtrate is concentrated to a volume of 50 ml and then chromatographed on silica gel (eluent: ethyl acetate/methanol 9:1). The product is recrystallized from ethyl acetate/n-hexane. There are obtained 2.22 g (53%) of tert-butyl 4-[2-(carbamoylmethyl)-1-cyclopropyl-5-fluoro-6-benzimidazolyl]-1-piperazinecarboxylate with a m.p. of 219°–220°.

Microanalysis $C_{21}H_{28}FN_5O_3$: Calc.: C 60.42, H 6.76, N 16.78. Found: C 60.26, H 6.88, N 16.31.

f) tert-Butyl 4-[2-(carbamoylmethyl)-1-cyclopropyl-5-fluoro-6-benzimidazolyl]-1-piperazinecarboxylate (980 mg, 2.53 mmol) is suspended in THF (15 ml) and treated with 1,1'-carbonyldiimidazole (760 mg, 2 mmol) and 1,8-diazabicyclo[5.4.0]undec-7-ene (0.2 ml). The reaction mixture is heated to 60° for 2 hours, whereby white crystals separate. The suspension is then cooled to 0°. The crystals are filtered off and recrystallized from ethanol. There are obtained 760 mg (73%) of tert-butyl 4-[5-cyclopropyl-8-fluoro-1,2,3,5-tetrahydro-1,3-dioxopyrimido-[1,6-a]benzimidazol-7-yl]-1-piperazinecarboxylate.

Microanalysis $C_{22}H_{26}FN_5O_4$ with 0.6 mol of ethanol: Calc.: C 59.41, H 6.67, N 14.69. Found: C 59.15, H 6.33, N 14.87.

g) tert-Butyl 4-[5-cyclopropyl-8-fluoro-1,2,3,5-tetrahydro-1,3-dioxopyrimido[1,6-a]benzimidazol-7-yl]-1-piperazinecarboxylate (471 mg, 1 mmol) is dissolved in trifluoroacetic acid (2 ml). After 1 hour at 25° the trifluoroacetic acid is distilled off. The residue is taken up in water (10 ml), treated with sodium hydrogen carbonate (168 mg, 2 mmol) and stirred at 25° for 2 hours. The suspension is cooled to 0°. The crystals are filtered off, washed in succession with in each case 5 ml of cold water and ethanol and recrystallized from ethanol/water (95/5). There are obtained 208 mg (60.6%) of 5-cyclopropyl-8-fluoro-7-(1-piperazinyl)-pyrimido[1,6-a]benzimidazole-1,3(2H,5H)-dione trifluoroacetate.

Microanalysis $C_{17}H_{18}FN_5O_2 \cdot CF_3COOH$: Calc.: C 49.89, H 4.19, N 15.31. Found: C 49.71, H 4.43, N 15.29.

EXAMPLE 3 a) 1-[5-(Ethylamino)-2-fluoro-4-nitrophenyl]-4-methylpiperazine (2.8 g, 10 mmol) is dissolved in methanol (200 ml) and hydrogenated with 5 percent palladium/carbon under hydrogen at normal pressure. The palladium/carbon is filtered off and the filtrate is evaporated under reduced pressure. The residue is dried in a high vacuum, dissolved in diethyl glycol ethyl ether (10 ml) and then treated with ethyl cyanoacetate (2.26 g, 20 mmol). The solution is heated to 160° for 4 hours. The solvent is then distilled off and the residue is taken up in an acetic acid/ether mixture (100 ml, 1:2). The crystals obtained are filtered off, dissolved in an ethyl acetate/-methanol mixture (6:4 and chromatographed on silica gel (eluent: ethyl acetate/methanol 6:4). The product is recrystallized from an ethyl acetate/acetonitrile mixture (9:1). There are obtained 1.17 g (39%) of 1-ethyl-5-fluoro-6-(4-methyl-1-piperazinyl)-2-benzimidazoleacetonitrile with a m.p. of 204°–206°.

Microanalysis $C_{16}H_{20}FN_5$: Calc.: C 63.77, H 6.69, N 23.24. Found: C 63.65, H 6.54, N 23.31.

b) 1-Ethyl-5-fluoro-6-(4-methyl-1-piperazinyl)-2-benzimidazoleacetonitrile (834 mg, 2.77 mmol) is dissolved in pyridine (20 ml) and triethylamine (2.8 g, 27.7 mmol). The solution is cooled to 0°. Subsequently, hydrogen sulfide is introduced during 30 minutes. The thus-obtained deep green solution is heated to 45° for 2 hours. The solvent is distilled off and the residue is dried in a high vacuum and then crystallized from acetonitrile. The crystals are filtered off, dissolved in an ethyl acetate/methanol mixture (10 ml, 1:1) and then chromatographed on silica gel (eluent: ethyl acetate/methanol 6:4). The product is recrystallized from ethyl acetate. There are obtained 745 mg (80%) of 1-ethyl-5-fluoro-6-[4-methyl-1-piperazinyl]-2-benzimidazolecarbothioamide.

Microanalysis $C_{16}H_{22}FN_5S\cdot 0.3\ H_2O$: Calc.: C 56.38, H 6.68, N 20.55. Found: C 56.32, H 6.76, N 20.41.

c) 1-Ethyl-5-fluoro-6-[4-methyl-1-piperazinyl]-2-benzimidazolecarbothioamide (120 mg, 0.36 mmol) is suspended in tetrahydrofuran (2 ml) and treated with carbonyldiimidazole (140 mg, 0.86 mmol). The reaction solution is heated to 68° for 6 hours, whereby white crystals separate. The suspension is cooled to 0°. The crystals are filtered off, suspended in methanol and, after one hour, again filtered off, washed with ether and dried in a high vacuum. There are obtained 22 mg (16.9%) of 5-ethyl-9-fluoro-3,5-dihydro-8-(4-methyl-1-piperazinyl)-3-thioxopyrimido[1,6-a]benzimidazol-1(2H)-one.

Microanalysis $C_{17}H_{20}FN_5OS\cdot 0.7\ H_2O$: Calc.: C 54.59, H 5.77, N 18.72. Found: C 54.37, H 5.84, N 18.64.

EXAMPLE 4 a) tert-Butyl 4-[2-carbamoylmethyl)-1-cyclopropyl-5-fluoro-6-benzimidazolyl]-1-piperazinecarboxylate (703 mg, 1.68 mmol) is heated to 50° for 72 hours with O-benzylhydroxylamine hydrochloride (806 mg, 5.05 mmol) in a water/ethanol mixture (5 ml, 1:1). The solvent is distilled off and the residue is stirred in water (20 ml). The crystals obtained are filtered off, washed with water and dried in a high vacuum. The product is recrystallized from ethyl acetate. There are obtained 317 mg (36%) of tert-butyl 4-[2-[[(benzyloxy)carbamoyl]-methyl]-1-cyclopropyl-5-fluoro-6-benzimidazolyl]-1-piperazinecarboxylate.

Microanalysis $C_{28}H_{34}FN_5O_4$: Calc.: C 64.23, H 6.55, N 13.38. Found: C 64.35, H 6.83, N 13.35.

b) tert-Butyl 4-[2-[[(benzyloxy)carbamoyl]methyl]-1-cyclopropyl-5-fluoro-6-benzimidazolyl]-1-piperazinecarboxylate (779 mg, 1.18 mmol) is dissolved in tetrahydrofuran (15 ml) and treated with N,N'-carbonyldiimidazole (480 mg, 2.96 mmol) and 1,8-diazabicyclo[5.4.0]-undec-7-ene (225 mg, 1.48 mmol). The suspension obtained is poured into water (200 ml) and then extracted with ethyl acetate. The organic phase is washed in succession with water and 10 percent sodium chloride solution and dried over magnesium sulfate. The solvent is evaporated under reduced pressure and the residue is chromatographed on silica gel (eluent: ethyl acetate/n-hexane 8:2). The product is crystallized from ethyl acetate/n-hexane. There are obtained 42 mg (5%) of tert-butyl 4-[2-(benzyloxy)-5-cyclopropyl-8-fluoro-1,2,3,5-tetrahydro-1,3-dioxopyrimido[1,6-a]benzimidazol-7-yl]-1-piperazinecarboxylate.

Microanalysis $C_{29}H_{32}FN_5O_5$: Calc.: C 63.38, H 5.87, N 12.74. Found: C 62.78, H 5.69, N 12.64.

c) tert-Butyl 4-[2-(benzyloxy)-5-cyclopropyl-8-fluoro-1,2,3,5-tetrahydro-1,3-dioxopyrimido[1,6-a]benzimidazol-7-yl]-1-piperazinecarboxylate (981 mg, 1.87 mmol) is dissolved in ethanol (250 ml) and hydrogenated with 5 percent palladium/carbon (200 mg) under hydrogen at normal pressure. The palladium/carbon is filtered off and washed with dimethylformamide (100 ml) at 100°. The combined filtrates are evaporated under reduced pressure. The residue is recrystallized from dimethylformamide. There are obtained 619 mg (72%) of tert-butyl 4-[5-cyclopropyl-8-fluoro-1,2,3,5-tetrahydro-2-hydroxy-1,3-dioxopyrimido[1,6-a]benzimidazol-7-yl]-1-piperazinecarboxylate.

Microanalysis $C_{22}H_{26}FN_5O_5$: Calc.: C 57.51, H 5.70, N 15.24. Found: C 57.27, H 5.65, N 15.38.

d) tert-Butyl 4-[5-cyclopropyl-8-fluoro-1,2,3,5-tetrahydro-2-hydroxy-1,3-dioxopyrimido[1,6-a]benzimidazol-7-yl]-1-piperazinecarboxylate (350 mg, 0.76 mmol) is treated with a 2.5N hydrochloric acid solution in dioxane (4 ml), whereby a white precipitate forms immediately. The suspension is stirred at room temperature (25°) for 18 hours. The separated crystals are filtered off and dissolved in water (10 ml). The solution is treated with active charcoal, then filtered and cooled to 0°. The separated crystals are filtered off, washed with ethanol and ether and dried in a high vacuum. There are obtained 176 mg (58%) of 5-cyclopropyl-8-fluoro-2-hydroxy-7-(1-piperazinyl)-pyrimido[1,6-a]benzimidazole-1,3(2H,5H)-dione hydrochloride.

Microanalysis $C_{17}H_{19}FN_5O_3$: Calc.: C 51.59, H 4.84, N 17.69. Found: C 51.27, H 5.11, N 17.54.

EXAMPLE 5 a) 5-Chloro-N-cyclopropyl-4-fluoro-2-nitroaniline (460 mg, 2 mmol) is heated to 80° for 40 hours with L-proline tert-butyl ester (342 mg, 2 mmol) and 1,8-diazabicyclo[5.4.0]undec-7-ene (304 mg, 2 mmol). The reaction mixture is then dissolved in a water/ethyl acetate mixture (1:1, 100 ml). The ethyl acetate phase is washed with 10 percent sodium chloride solution, dried over magnesium sulfate and evaporated under reduced pressure. The residue is chromatographed on silica gel (eluent: hexane/ethyl acetate 8:2). The product is crystallized from ether/n-hexane. There are obtained 94 mg (13%) of tert-butyl rac-1-[5-(cyclopropylamino)-2-fluoro-4-nitro-phenyl]pyrrole-2-carboxylate with a m.p. of 142°–143°.

Microanalysis $C_{18}H_{24}FN_3O_4$: Calc.: C 59.17, H 6.62, N 11.50. Found: C 59.23, H 6.62, N 11.52.

b) Analogous to Example 2d), from tert-butyl rac-1-[5-(cyclopropylamino)-2-fluoro-4-nitrophenyl]pyrrole-2-carboxylate there is obtained in a yield of 56% ethyl rac-6-[2-(tert-butoxycarbonyl)-1-pyrrolidinyl]-1-cyclopropyl-5-fluoro-2-benzimidazoleacetate with a m.p. of 93°–96°.

Microanalysis $C_{23}H_{30}FN_3O_4$: Calc.: C 64.02, H 7.01, N 9.74. Found: C 64.47, H 7.16, N 9.77.

c) Analogous to Example 2e), from ethyl rac-6-[2-(tert-butoxycarbonyl)-1-pyrrolidinyl]-1-cyclopropyl-5-fluoro-2-benzimidazoleacetate there is obtained in a yield of 34% tert-butyl rac-1-[2-(carbamoylmethyl)-1-cyclopropyl-5-fluoro-6-benzimidazolyl]-2-pyrrolidinecarboxylate with a m.p. of 176°–178°.

Microanalysis $C_{21}H_{27}FN_4O_3$: Calc.: C 62.67, H 6.76, N 13.92. Found: C 62.40, H 6.86, N 13.60.

d) Analogous to Example 2f), from tert-butyl rac-1-[2-(carbamoylmethyl)-1-cyclopropyl-5-fluoro-6-benzimidazolyl]-2-pyrrolidinecarboxylate there is obtained in a yield of 60% tert-butyl rac-1-[5-cyclopropyl-8-fluoro-2,3-dihydro-1,3-dioxopyrimido[1,6-a]benzimidazol-7(1H)-yl]-2-pyrrolidinecarboxylate with a m.p. of 226°–227°.

Microanalysis $C_{22}H_{25}FN_4O_4 \cdot 0.25$ THF Calc.: C 61.87, H 6.10, N 12.55. Found: C 61.77, H 6.38, N 12.62.

EXAMPLE 6 a) tert-Butyl 4-[2-(benzyloxy)-5-cyclopropyl-8-fluoro-1,2,3,5-tetrahydro-1,3-dioxopyrimido[1,6-a]benzimidazol-7-yl]-1-piperazinecarboxylate (580 mg, 1.05 mmol) is treated with 33 percent hydrobromic acid in glacial acetic acid (5 ml). After 18 hours at room temperature the separated crystals are filtered off, washed with glacial acetic acid and recrystallized from methanol. The crystals are then dissolved in a water/ethanol mixture (2:1, 50 ml). The pH is adjusted to 8 using 1N sodium hydroxide solution, whereby white crystals separate. The crystals are filtered off, washed with water and dried in a high vacuum. There are obtained 417 mg (88%) of 2-(benzyloxy)-5-cyclopropyl-8-fluoro-7-(1-piperazinyl)pyrimido[1,6-a]benzimidazole-1,3(2H,5H)-dione.

Microanalysis $C_{24}H_{24}FN_5O_3$: Calc.: C 64.13, H 5.38, N 15.58. Found: C 63.81, H 5.68, N 15.54.

b) Z-(L)-Alanine (223 mg, 1 mmol) is dissolved in dichloromethane (10 ml) and treated at 0° with dicyclohexylcarbodiimide (103 mg, 0.5 mmol). After 30 minutes the crystals are filtered off and washed with a small amount (30 ml) of dichloromethane. The filtrate is treated with a solution of 2-(benzyloxy)-5-cyclopropyl-8-fluoro-7-(1-piperazinyl)pyrimido[1,6-a]benzimidazole-1,3(2H,5H)-dione (112 mg, 0.25 mmol) in DMF (5 ml). After 2 hours the solvent is distilled off. The residue is recrystallized from methanol. There are obtained 142 mg (86%) of benzyl [(S)-1-[[4-[2-(benzyloxy)-5-cyclopropyl-8-fluoro-1,2,3,5-tetrahydro-1,3-dioxopyrimido[1,6-a]benzimidazol-7-yl]-1-piperazinyl]carbonyl]ethyl]carbamate.

MS: 653(M).

c) Benzyl [(S)-1-[[4-[2-(benzyloxy)-5-cyclopropyl-8-fluoro-1,2,3,5-tetrahydro-1,3-dioxopyrimido[1,6-a]benzimidazol-7-yl]-1-piperazinyl]carbonyl]ethyl]carbamate (127 mg, 0.194 mmol) is dissolved in DMF (15 ml) and hydrogenated over 5 percent Pd/C. After completion of the reduction the catalyst is filtered off and the filtrate is evaporated. The residue is taken up in methanol (50 ml) and treated with active charcoal. After filtering off the charcoal the filtrate is concentrated to a volume of 25 ml. The separated crystals are filtered off. There are obtained 62 mg (84%) of 7-(4-L-alanyl-1-piperazinyl)-5-cyclopropyl-8-fluoro-2-hydroxypyrimido[1,6-a]benzimidazole-1,3(2H,5H)-dione.

Microanalysis $C_{20}H_{23}FN_6O_4 \cdot 0.25$ $CH_3OH$: Calc.: C 55.47, H 5.52, N 19.17. Found: C 55.15, H 5.76, N 19.18.

EXAMPLE 7 a) A solution of ethyl rac-6-[2-(tert-butoxycarbonyl)-1-pyrrolidinyl]-1-cyclopropyl-5-fluoro-2-benzimidazoleacetate (1.647 g, 3.82 mmol) in ethanol (15 ml) is treated with a 1N ethanolic solution of hydroxylamine (9.54 ml, 9.54 mmol) and with a 1N ethanolic sodium methylate solution (1.91 ml, 1.91 mmol). After one hour the solvent is distilled off and the residue is dissolved in water. The pH is adjusted to 5.5 with 1N hydrochloric acid. This solution is extracted with ethyl acetate and the organic phase is washed with water, dried (magnesium sulfate) and concentrated. The residue is recrystallized from ethyl acetate. The crystals obtained are dissolved in tetrahydrofuran (30 ml) and treated with 1,8-diazabicyclo[5.4.0]undec-7-ene (377 mg, 2.5 mmol) and benzyl bromide (462 mg, 2.7 mmol). After 4 hours the reaction solution is diluted with ethyl acetate (150 ml) and washed with water (100 ml) and subsequently with 10 percent sodium chloride solution (100 ml). The organic phase is dried (magnesium sulfate) and concentrated. The residue is recrystallized from ether/n-hexane. There are obtained 643 mg (33%) of 1-[2-[[(benzyloxy)carbamoyl]methyl]-1-cyclopropyl-5-fluoro-6-benzimidazolyl]-L-proline tert-butyl ester.

Microanalysis $C_{28}H_{33}FN_4O_4$: Calc.: C 66.13, H 6.54, N 11.01. Found: C 65.99, H 6.86, N 11.14.

b) Analogous to Example 4b), from 1-[2-[[(benzyloxy)carbamoyl]methyl]-1-cyclopropyl-5-fluoro-6-benzimidazolyl]-L-proline tert-butyl ester there is obtained in a yield of 78% 1-[2-(benzyloxy)-5-cyclopropyl-8-fluoro-1,2,3,5-tetrahydro-1,3-dioxopyrimido[1,6-a]benzimidazol-7-yl]-L-proline tert-butyl ester.

MS: 534(M).

c) Analogous to Example 4c), from 1-[2-(benzyloxy)-5-cyclopropyl-8-fluoro-1,2,3,5-tetrahydro-1,3-dioxopyrimido[1,6-a]benzimidazol-7-yl]-L-proline tert-butyl ester there is obtained in a yield of 81% 1-[5-cyclopropyl-8-fluoro-1,2,3,5-tetrahydro-2-hydroxy-1,3-dioxopyrimido[1,6-a]benzimidazol-7-yl]-L-proline tert-butyl ester.

Microanalysis $C_{22}H_{25}FN_4O_5$: Calc.: C 59.45, H 5.67, N 12.61. Found: C 59.03, H 5.54, N 12.51.

EXAMPLE 8 a) Analogous to Example 1d), from N-acetylpiperazine and 5'-chloro-N-ethyl-4'-fluoro-2'-nitroacetanilide there is obtained in a yield of 76% N-ethyl-4'-fluoro-5'-(4-acetyl-1-piperazinyl)-2'-nitroacetanilide with a m.p. of 129°–131°.

Microanalysis $C_{16}H_{21}FN_4O_4$: Calc.: C 54.54, H 6.01, N 15.90. Found: C 54.33, H 6.18, N 15.80.

b) A solution of N-ethyl-4'-fluoro-5'-(4-acetyl-1-piperazinyl)-2'-nitroacetanilide (8.4 g, 23.8 mmol) in methanol (100 ml) is treated with potassium hydroxide solution (13.3 g, 238 mmol in 20 ml). The solution is heated under reflux for 3 hours and then poured on to ice. The separated crystals are filtered off (m.p. 129°–131°), suspended in dioxan/water 1:1 (200 ml) and treated with di-tert-butyl dicarbonate (4.44 g, 20.35 mmol) and sodium bicarbonate (1.71 g, 20.35 mmol). After 24 hours the reaction mixture is evaporated. The residue is taken up in ethyl acetate (500 ml) and washed with water (500 ml) and 10 percent sodium chloride solution. The organic phase is dried over magnesium sulfate and concentrated. The residue is crystallized from ethyl acetate/n-hexane. There are obtained 6.33 g (72%) of tert-butyl 4-[5-(ethylamino)-2-fluoro-4-nitrophenyl]-1-piperazinecarboxylate with a m.p. of 155°-157°.

c) Analogous to Example 2d), from tert-butyl 4-[5-(ethylamino)-2-fluoro-4-nitrophenyl]-1-piperazinecarboxylate there is obtained in a yield of 67% ethyl 6-[4-tert-butoxycarbonyl)-1-piperazinyl]-1-ethyl-5-fluoro-2-benzimidazoleacetate with a m.p. of 131°-133°.

Microanalysis $C_{22}H_{31}FN_4O_4$: Calc.: C 60.81, H 7.19, N 12.89. Found: C 60.73, H 7.44, N 12.88.

d) Analogous to Example 2e), from ethyl 6-[4-tert-butoxycarbonyl)-1-piperazinyl]-1-ethyl-5-fluoro-2-benzimidazoleacetate there is obtained a yield of 36% tert-butyl 4-[2-carbamoylmethyl)-1-ethyl-5-fluoro-6-benzimidazolyl]-1-piperazinecarboxylate with a m.p. of 162°-164°.

MS: 405(M).

e) Analogous to Example 2f), from tert-butyl 4-[2-(carbamoylmethyl)-1-ethyl-5-fluoro-6-benzimidazolyl]-1-piperazinecarboxylate there is obtained in a yield of 67% tert-butyl 4-(5-ethyl-8-fluoro-1,2,3,5-tetrahydro-1,3-dioxopyrimido[1,6-a]benzimidazol-7-yl)-1-piperazinecarboxylate with a m.p. of 270°-273°.

Microanalysis $C_{21}H_{26}FN_5O_4$: Calc.: C 58.46, H 6.07, N 16.23. Found: C 58.18, H 6.30, N 16.16.

f) Analogous to Example 2g), from tert-butyl 4-(5-ethyl-8-fluoro-1,2,3,5-tetrahydro-1,3-dioxopyrimido[1,6-a]benzimidazol-7-yl)-1-piperazinecarboxylate there is obtained in a yield of 70% 5-ethyl-8-fluoro-7-(1-piperazinyl)pyrimido[1,6-a]benzimidazole-1,3(2H,5H)-dione with a m.p. of 264°-266°.

Microanalysis $C_{16}H_{18}FN_5O_2.0.2$ $CH_3OH$: Calc.: C 57.61, H 5.61, N 20.74. Found: C 57.44, H 5.49, N 20.85.

EXAMPLE 9 a) Analogous to Example 2d), from 1-(5-ethylamino)-2-fluoro-4-nitrophenyl)-4-methylpiperazine there is obtained in a yield of 30%, ethyl 1-ethyl-5-fluoro-6-(4-methyl-1-piperazinyl)-2-benzimidazoleacetate with a m.p. of 142°-144°.

Microanalysis $C_{18}H_{25}FN_4O_2$: Calc.: C 62.05, H 7.23, N 16.08. Found: C 61.68, H 7.31, N 16.09.

b) Analogous to Example 2e), from ethyl 1-ethyl-5-fluoro-6-(4-methyl-1-piperazinyl)-2-benzimidazoleacetate there is obtained 1-ethyl-5-fluoro-6-(4-methyl-1-piperazinyl)-2-benzimidazoleacetamide. From this intermediate there is obtained analogous to Example 4a), in a yield of 35% (over both steps), 2-[[(benzyloxy)carbamoyl]methyl]-1-ethyl-5-fluoro-6-(4-methyl-1-piperazinyl)-benzimidazole with a m.p. of 165°-168° (ethyl acetate).

Microanalysis $C_{23}H_{28}FN_5O_2$: Calc.: C 64.92, H 6.63, N 16.46. Found: C 64.92, H 6.85, N 16.36.

c) Analogous to Example 4b), from 2-[[(benzyloxy)carbamoyl]methyl]-1-ethyl-5-fluoro-6-(4-methyl-1-piperazinyl)-benzimidazole there is obtained, in a yield of 54%, 2-(benzyloxy)-5-ethyl-8-fluoro-7-(4-methyl-1-piperazinyl)pyrimido[1,6-a]benzimidazole-1,3(2H,5H)-dione with a m.p. of 250°-252° (methanol).

Microanalysis $C_{24}H_{26}FN_5O_3$: Calc.: C 63.85, H 5.80, N 15.51. Found: C 63.64, H 6.13, N 15.43.

d) Analogous to Example 4c), from 2-(benzyloxy)-5-ethyl-8-fluoro-7-(4-methyl-1-piperazinyl)pyrimido[1,6-a]benzimidazole-1,3(2H,5H)-dione there is obtained, in a yield of 53%, 4-ethyl-8-fluoro-2-hydroxy-7-(4-methyl-1-piperazinyl)pyrimido[1,6-a]benzimidazole-1,3(2H,5H)-dione.

Microanalysis $C_{17}H_{20}FN_5O_3.0.2$ DMF: Calc.: C 56.22, H 5.74, N 19.37. Found: C 56.05, H 5.90, N 19.40.

EXAMPLE 10 a) Analogous to Example 2d), from p-nitrobenzyl 3-ethoxy-3-iminopropanoate hydrochloride and tert-butyl 4-[5-(cyclopropylamino)-2-fluoro-4-nitrophenyl]-1-piperazinecarboxylate there is obtained, in a yield of 44%, p-nitrobenzyl 6-[4-(tert-butoxycarbonyl)-1-piperazinyl]-1-cyclopropyl-5-fluoro-2-benzimidazoleacetate.

Microanalysis $C_{28}H_{32}FN_5O_6$: Calc.: C 60.75, H 5.83, N 12.65. Found: C 60.81, H 6.11, N 12.54.

b) A solution of p-nitrobenzyl 6-[4-(tert-butoxycarbonyl)-1-piperazinyl]-1-cyclopropyl-5-fluoro-2-benzimidazole acetate (553 mg, 1 mmol) in THF (50 ml) is treated in succession at 0° with triethylamine (300 mg, 3 mmol) and chloroacetyl isocyanate (298 mg, 2.5 mmol). After stirring for 20 hours the solvent is distilled off and the residues is taken up in ethyl acetate and washed in succession with water (50 ml) and 10 percent sodium chloride solution (50 ml). The organic phase is dried over magnesium sulfate and the solvent is evaporated. The residue is recrystallized from ethyl acetate. There are obtained 373 mg (59%) of p-nitrobenzyl 5-cyclopropyl-8-fluoro-1,2,3,4-tetrahydro-1,3-dioxo-7-[4-(tert-butoxycarbonyl)-1-piperazinyl]pyrimido[1,6-a]benzimidazole-4-carboxylate.

Microanalysis $C_{30}H_{31}FN_6O_8$: Calc.: C 57.87, H 5.02, N 13.50. Found: C 57.50, H 5.04, N 13.38.

c) A solution of p-nitrobenzyl 5-cyclopropyl-8-fluoro-1,2,3,4-tetrahydro-1,3-dioxo-7-[4-tert-butoxycarbonyl)-1-piperazinyl]pyrimido[1,6-a]benzimidazole-4-carboxylate (1.758 g, 2.82 mmol) in acetonitrile (250 ml) is treated in succession with sodium iodide (846 mg, 5.65 mmol) and trimethylchlorosilane (1.23 g, 11.28 mmol). After one hour at 80° the suspension obtained is cooled to 0°. The crystals are filtered off and taken up in an ethanol/water mixture (2:8, 250 ml). The pH is adjusted to 8.0 with a sodium bicarbonate solution. The suspension is cooled to 0° and the pale yellow crystals are filtered off. The filter residue is suspended in ethanol. The crystals are filtered off and washed with ether. There are obtained 1.10 g (75%) of p-nitrobenzyl 5-cyclopropyl-8-fluoro-1,2,3,4-tetrahydro-1,3-dioxo-7-(1-piperazinyl)pyrimido-[1,6-a]benzimidazole-4-carboxylate.

Microanalysis $C_{25}H_{23}FN_6O_6$: Calc.: C 57.47, H 4.44, N 16.08. Found: C 57.13, H 4.48, N 15.97.

d) A solution of p-nitrobenzyl 5-cyclopropyl-8-fluoro-1,2,3,4-tetrahydro-1,3-dioxo-7-(1-piperazinyl)-pyrimido[1,6-a]benzimidazole-4-carboxylate (122 mg, 0.234 mmol) in DMF (30 ml) is hydrogenated over 5 percent Pd/C. After completion of the hydrogenation the catalyst is filtered off and the filtrate is treated with fuller's earth, filtered and concentrated to a volume of 5 ml. The separated crystals are filtered off. There are obtained 62 mg (68%) of the sodium salt of 5-cyclopropyl-8-fluoro-1,2,3,4-tetrahydro-1,3-dioxo-7-(1-piperazinyl)pyrimido[1,6-a]benzimidazole-4-carboxylic acid.

MS: 343 (M-CO$_2$), 44 (CO$_2$).

The crystals are taken up in DMF (10 ml) and treated with a saturated sodium bicarbonate solution (1 ml). The solvent is distilled off and the residue is chromatographed with water on a reversed phase (column RP8). There are obtained 39 mg (40%) of the above product.

MS: 343 (M-CO$_2$), 44 (CO$_2$).

EXAMPLE 11

Analogous to Example 9, from tert-butyl 4-[2-(carbamoylmethyl)-1-ethyl-5-fluoro-6-benzimidazolyl]-1-piperazinecarboxylate (from Example 8d) there is obtained, after cleaving off the tert-butoxycarbonyl group using 2.5N HCl/dioxane (analogous to Example 4d), 5-ethyl-8-fluoro-2-hydroxy-7-(1-piperazinyl)-pyrimido[1,6-a]benzimidazole-1,3(2H,5H)-dione hydrochloride.

Microanalysis $C_{16}H_{19}ClFN_5O_3$: Calc.: C 50.07, H 4.99, N 18.25. Found: C 50.94, H 5.22, N 18.47.

EXAMPLE 12 a) Ethyl 6-[4-(tert-butoxycarbonyl)-1-piperazinyl]1-cyclopropyl-5-fluoro-2-benzimidazoleacetate (1.8 g, 4 mmol; from Example 2d) and tert.butyl carbazate (21 g, 16 mmol) are dissolved in pyridine (40 ml) and stirred at 115° under argon for 65 hours. The reaction solution is concentrated and triturated with 50 ml of ether. The separated product is filtered off under suction and dried. There is obtained tert-butyl 3-[[6-[4-(tert-butoxycarbonyl)-1-piperazinyl]-1-cyclopropyl-5-fluoro-2-benzimidazolyl]acetyl]carbazate. Yield: 0.49 g (23%); m.p. 202°-203°.

Microanalysis $C_{26}H_{37}FN_6O_5$: Calc.: C 58.63, H 7.00, N 15.78. Found: C 58.44, H 7.15, N 15.66.

b) tert-Butyl 3-[ ]6-[4-(tert-butoxycarbonyl)-1-piperazinyl]-1-cyclopropyl-5-fluoro-2-benzimidazolyl]acetyl]carbazate (0.40 g, 0.76 mmol) is dissolved in THF (15 ml) and treated with 1,1'-carbonyldiimidazole (0.24 g, 1.5 mmol) and DBU (3 drops). The solution obtained is stirred at 60° C. for 2 hours and thereafter concentrated on a rotary evaporator. The residue is dissolved in ethyl acetate and then chromatographed on silica gel (eluent:ethyl acetate/hexane 4:1). The product is recrystallized from ethyl acetate/ether. There is obtained tert-butyl 7-[4-(tert-butoxycarbonyl)-1-piperazinyl]-5-cyclopropyl-8-fluoro-3,5-dihydro-1,3-dioxopyrimido[1,6-a]benzimidazole-2(1H)-carbamate. Yield: 85 mg (20%); m.p. 219°-220°.

Microanalysis $C_{27}H_{35}FN_6O_6$: Calc.: C 58.05, H 6.32, N 15.04. Found: C 57.87, H 6.36, N 14.69.

c) tert-Butyl 7-[4-(tert-butoxycarbonyl)-1-piperazinyl]-5-cyclopropyl-8-fluoro-3,5-dihydro-1,3-dioxopyrimido-[1,6-a]benzimidazol-2(1H)-carbamate (0.145 g, 0.26 mmol) is dissolved in 1 ml of trifluoroacetic acid and stirred at room temperature for 2 hours. The reaction solution is concentrated, treated with 1 ml of H₂O, adjusted to pH 8 with saturated aqueous NaHCO₃ solution and stirred at room temperature for 1 hour. The suspension is cooled to 0° and suction filtered. The product is chromatographed on silica gel (eluent: CHCl₃/EtOH/NH₄OH 80:20:1) and recrystallized from ethanol. There is obtained 2-amino-5-cyclopropyl-8-fluoro-7-(1-piperazinyl)pyrimido[1,6-a]benzimidazole-1,3(2H,5H)-dione. Yield: 43 mg (46%); m.p. 232°-234°.

Microanalysis $C_{17}H_{19}FN_6O_2$; 0.3 EtOH: Calc.: C 56.70, H 5.62, N 22.58. Found: C 56.40, H 5.77, N 22.67.

EXAMPLE 13 a) Analogous to Example 12a), from ethyl 6-[4-(tert-butoxycarbonyl)-1-piperazinyl]-1-cyclopropyl-5-fluoro-2-benzimidazoleacetate and tert-butyl 2-methyl-carbazate there is obtained, in a yield of 33%, tert-butyl-4-[2-[[[2-(tert-butoxycarbonyl)-2-methyl-hydrazino]carbonyl]methyl]-1-cyclopropyl-5-fluoro-6-benzimidazolyl]-1-piperazine-carboxylate with a m.p. of 180°-182°.

MS: 546 (M); 446 [M-(isobutene+CO₂)].

b) Analogous to Example 12b), starting from tert-butyl 4-[2-[[[2-(tert-butoxycarbonyl)-2-methylhydrazino]carbonyl]methyl]-1-cyclopropyl-5-fluoro-6-benzimidazolyl]-1-piperazinecarboxylate there is obtained, in a yield of 59%, tert-butyl 7-[4-(tert-butoxycarbonyl)-1-piperazinyl]- 5-cyclopropyl-8-fluoro-3,5-dihydro-N-methyl-1,3-dioxopyrimido-[1,6-a]benzimidazole-2-carbamate with a m.p. of 224°-225°.

MS: 573 (M+H)⁺.

c) Analogous to Example 12c), starting from tert-butyl 7-[4-(tert-butoxycarbonyl)-1-piperazinyl]-5-cyclopropyl-8-fluoro-3,5-dihydro-N-methyl-1,3-dioxopyrimido[1,6-a]benzimidazole-2-carbamate there is obtained, in a yield of 43%, 5-cyclopropyl-8-fluoro-2-(methylamino)-7-(1-piperazinyl)pyrimido[1,6-a]benzimidazole-1,3(2H,5H)-dione with a m.p. of 228°-230°.

Microanalysis $C_{18}H_{21}FN_6O_2$: Calc.: C 58.05, H 5.68, N 22.57. Found: C 57.95, H 5.81, N 22.18.

EXAMPLE 14 a) Analogous to Example 12a), from ethyl 6-[4-(tert-butoxycarbonyl)-1-piperazinyl]-1-cyclopropyl-5-fluoro-2-benzimidazoleacetate and hydrazine hydrate there is obtained tert-butyl 4-[2-[[(hydrazino)carbonyl]-methyl]-1-cyclopropyl-5-fluoro-6-benzimidazolyl]-1-piperazine-carboxylate with a m.p. of 172°-173°.

Microanalysis $C_{21}H_{29}FN_6O_3$: Calc.: C 58.32, H 6.76, N 19.43. Found: C 57.86, H 6.91, N 19.20.

b) A solution of tert-butyl 4-[2-[[(hydrazino)carbonyl]methyl]-1-cyclopropyl-5-fluoro-6-benzimidazolyl]-1-piperazine-carboxylate (0.43 g) in methanol (22 ml) is stirred at 50° with a 35% aqueous formaldehyde solution (0.102 g); subsequently sodium borohydride (46 mg) is added. This procedure is carried out 3 times. The reaction mixture is evaporated and the raw material crystallized from ethyl acetate. 0.325 g (70%) of tert-butyl 4-[2-[[[2-(dimethylhydrazino)carbonyl]methyl]-1-cyclopropyl-5-fluoro-6-benzimidazolyl]-1-piperazine-carboxylate are obtained with a m.p. of 179°-181°.

MS: 460 (M)

c) Analogous to Example 12b), starting from tert-butyl 4-[2-[[[2-(dimethylhydrazino)]carbonyl]methyl]-1-cyclopropyl-5-fluoro-6-benzimidazolyl]-1-piperazinecarboxylate there is obtained tert-butyl 4-[5-cyclopropyl-8-fluoro-1,2,3,5-tetrahydro-2-(dimethylamino)-1,3-dioxopyrimido[1,6-a]benzimidazol-7-yl]-1-piperazinecarboxylate with a m.p. of 201°-203°.

Microanalysis $C_{24}H_{31}FN_6O_4$: Calc.: C 59.25, H 6.42, N 17.27. Found: C 59.13, H 7.10, N 17.73.

d) Analogous to Example 12c), starting from tert-butyl 4-[5-cyclopropyl-8-fluoro-1,2,3,5-tetrahydro-2-(dimethylamino)-1,3-dioxopyrimido[1,6-a]benzimidazol-7-yl]-1-piperazine-carboxylate there is obtained 5-cyclopropyl-2-(dimethylamino)-8-fluoro-7-(1-piperazinyl)pyrimido[1,6-a]benzimidazole-1,3(2H,5H)-dione with a m.p. of 207°-209°.

Microanalysis $C_{19}H_{23}FN_6O_2$: Calc.: C 59.06, H 6.00, N 21.75. Found: C 58.12, H 6.17, N20.75.

EXAMPLE 15 a) Analogous to example 2b), starting from 5-chloro-n-cyclopropyl-4-fluoro-2-nitroaniline and N-methyl piperazine there is obtained N-cyclopropyl-4-fluoro-5-(4-methyl-1-piperazinyl)-2-nitroaniline with a mp of 130°.

Microanalysis: $C_{14}H_{19}FN_4O_2$: Calc.: C 57.13, H 6.51, N 19.04. Found: C 57.15, H 6.61, N 19.02.

b) Analogous to example 2d), starting from N-cyclopropyl-4-fluoro 5-(4-methylpiperazinyl)-2-nitroaniline there is obtained ethyl 1-cyclopropyl-5-fluoro-6-(4-methyl-1-piperazinyl)-2-benzimidazole acetate with a mp of 128°.

Microanalysis: $C_{19}H_{25}FN_4O_2$: Calc: C 63.32, H 6.99, N 15.54. Found: C $_{63.15}$, H 7.12, N 15.67.

c) Analogous to example 2e), starting from ethyl 1-cyclopropyl-5-fluoro-6-(4-methyl-1-piperazinyl)-2-benzimidazole acetate there is obtained 1-cyclopropyl-5-fluoro-6-(4-methyl-1-piperazinyl)-2-benzimidazole acetamide hydrochloride with a mp of 254°-258°.

Microanalysis: $C_{17}H_{23}ClFN_5O + 0.25$ $C_2H_5OH$: Calc: C 55.40, H 6.51, N 18.46, Cl 9.35. Found: C 55.42, H 6.55, N 18.39, Cl 9.44.

d) Analogous to example 4a), starting from 1-cyclopropyl-5-flouro-6-(4-methyl-1-piperazinyl)-2-benzimidazole acetamide there is obtained N-(benzyloxy)-1-cyclopropyl-5-fluoro-6-(4-methyl-1-piperazinyl)-2-benzimidazole acetamide with a mp of 158°.

Microanalysis: $C_{24}H_{28}FN_5O_2$: Calc: C 65.89, H 6.45, N 16.01. Found: C 65.71, H 6.48, N 16.03.

e) Analogous to example 4b), starting from N-(Benzyloxy)-1-cyclopropyl-5-fluoro-6-(4-methyl-1-piperazinyl)-2-benzimidazole acetamide there is obtained 2-(Benzyloxy)-5-cyclopropyl-8-fluoro-7-(4-methyl-1-piperazinyl)1H pyrimido[1,6-a]benzimidazole-1,3(2H,5H)dione with a m.p. of >250°.

Microanalysis: $C_{25}H_{26}FN_5C_2$: Calc: C 64.78, H 5.65, N 15.11. Found: 63.19, H 6.05, N 14.39.

f) Analogous to example 4c), starting from 2-(Benzyloxy)-5-cyclopropyl-8-fluoro-7-(4-methyl-1-piperazinyl)-1H-pyrimido[1,6-a]benzimidazole-1,3(2H,5H)-dione there is obtained 5-cyclopropyl-8-fluoro-2-hydroxy-7-(4-methyl-1-piperazinyl)-1H-pyrimido-[1,6-a]benzimidazole-1,3(2H,5H)-dione with a m.p. of 265°-268°.

Microanalysis: $C_{18}H_{20}FN_5C_3$: Calc.: C 57.90, H 5.40, N 18.76. Found: 57.14, H 5.30, N 18.25.

EXAMPLE 16

Pentafluoronitrobenzene (10 g, 46.9 mmol) is cooled to 0° C. and treated dropwise with 1-methylpiperazine (5.2 ml, 47 mmol) in triethylamine (14 ml, 94 mmol). After 30 minutes at 0° C., the reaction mixture is allowed to reach room temperature. After one hour, the orange suspension is diluted with water (100 ml) and extracted with ether (3×100 ml). The combined organic layers are washed with saturated aqueous sodium chloride solution (100 ml), dried with magnesium sulfate and evaporated. Recrystallization from n-hexane-ether (1:1) yields 10 g of 1-methyl-4-(2,3,5,6-tetrafluoro-4-nitrophenyl)piperazine as red-brown crystals (73%): mp: 77°-78° C.; NMR(CDCl$_3$):2.35(s,3H),2.54 (m,4H),3.44(m,4H).

Microanalysis: $C_{11}H_{11}F_4N_3O_2$: Calc: C:45.06, H:3.78, N:14.33, F:25.92%. Found: C:44;97, H:3.86, N:14.37, F:26.50%.

1-Methyl-4-(2,3,5,6-tetrafluoro-4-nitrophenyl)-piperazine(9.4 g,34.15 mmol) is suspended in triethylamine (20 ml) and treated dropwise with cyclopropylamine (2.9 ml, 41 mmol). During the addition, the temperature is maintained below +10° C. The reaction mixture is stirred at room temperature overnight, then evaporated, suspended in ether (200 ml) and sequentially washed with 1N aqueous sodium hydroxide solution (45 ml), saturated aqueous sodium chloride solution, then dried (magnesium sulfate) and evaporated. Recrystallization from n-hexane yields 9.7 g of N-cyclopropyl-2,4,5-trifluoro-3-(4-methyl-1-piperazinyl)-6-nitroaniline as orange crystals (86%): mp:75° C.; NMR (CDCl$_3$): 0.55 (m,2H),0.75(m,2H),2.35(s,3H),2.53(m,4H),2.92(m,1H),-3.40(m,4H), 6.65(s,1H).

Microanalysis: $C_{14}H_{17}F_3N_4O_2$: Calc: C:50.91, H:5.19, N:16.96%. Found: C:51.07, H:5.27, N:16.95%.

N-Cyclopropyl-2,4,5-trifluoro-3-(4-methyl-1-piperazinyl)-6-nitroaniline (9.5 g,28.8 mmol) and benzylamine (5.7 ml,51.19 mmol) are suspended in triethylamine (100 ml) and warmed to 90° C. for two hours. After cooling, the reaction mixture is concentrated and chromatographed on silica gel (eluent: ethyl acetate), yielding, after crystallization (ethyl acetate), 11.8 of 5-(benzylamino)-N-cyclopropyl-2,4-difluoro-3-(4-methyl-1-piperazinyl)-6-nitroaniline as purple crystals (98%): mp 88°-90° C.; NMR (CDCl$_3$): 0.55 (m, 2H), 0.75(m, 2H),2.34(s,3H),2.50(m,4H), 2.96 (m,1H), 3.37(m,4H),4.54(m,2H),7.21-7.36(m,5H),7.61(s,1H),7.82 (m,1H).

5-(Benzylamino)-N-cyclopropyl-2,4-difluoro-3-(4-methyl-1-piperazinyl)-6-nitroalinine (11.5 g,27.5 mmol) is dissolved in concentrated acetic acid (200 ml). Zinc powder (23 g) is added in 1 g portions while the temperature is maintained below 20° C. After stirring for 1 hour, the yellow suspension is filtered and concentrated. The unstable oily residue is rapidly dissolved in dimethylformamide (50 ml) under argon and treated portionwise with ethylamidocarboxy acetimidate hydrochloride (11.5 g, 68.8 mMol). The resulting suspension is stirred at 50° C. for 24 hours. After cooling, ethyl acetate (200 ml) is added and the pH is adjusted to 8-9 with a saturated aqueous sodium bicarbonate solution. The aqueous layer is extracted with ethyl acetate (3×100 ml). The combined organic layers are dried (magnesium sulfate), concentrated and chromatographed on silica gel, (eluent: 5% methanol-dichloromethane). The resulting solid is crystallized (tetrahydrofuran) yielding 4.4 g of 4-(benzylamino)-1-cyclopropyl-5,7-difluoro-6-(4-methyl-1-piperazinyl)-2-benzimidazoleacetamide as colorless crystals (35%): mp: 157°-159° C.; NMR (DMSO-d$_6$): 1.07 (m,4H),2.22(s,3H),2.43(m,4H), 3.07(m,4H),3.28(m,1H),3.82(s,2H),4.78(d,J=6.5 Hz,2H),5.53(m,1H), 7.12-7.36(m,6H),7.66(s,1H).

Microanalysis: $C_{24}H_{28}F_2N_6O$: Calc: C:63.42, H:6.21, N:18.49%. Found: C:63.63, H:6.43, N:18.40%.

4-(Benzylamino)-1-cyclopropyl-5,7-difluoro-6-(4-methyl-1-piperazinyl)-2-benzimidazoleacetamide (4.4 g, 9.7 mmol) and O-benzyl-hydroxylamine hydrochloride (6.2 g, 38.8 mmol) are suspended in water-ethanol (1:1; 100 ml) and warmed to 60° C. for two days. After cooling, the pH is adjusted to 5-6 with saturated aqueous sodium bicarbonate solution and the resulting solution extracted with ethyl acetate. The combined organic layers are dried (magnesium sulfate), concentrated and chromatographed on silica gel (eluent: 5% then 15% methanol-dichloromethane), affording 2.6 g of 2-[7-benzylamino-1-cyclopropyl-4,6-difluoro-5-(4-methyl-piperazin-1-yl)-1H-benzimidazol-2-yl]-N-benzyloxy-acetamide (48%): NMR (CDCl$_3$): 1.04 (m,4H),2.42(s,3H),2.65 (m,4H), 3.27 (m,5H), 3.93(s,2H),4.67(s,2H),4.89(s,2H),7.20-7.39(m,10H), 10.47(s,1H).

Microanalysis: $C_{31}H_{34}F_2N_6O_2$: Calc: C:66.41, H:6.11, N:14.99%. Found: C:66.39, H:6.11, N:15:13%.

2-[7-Benzylamino-1-cyclopropyl-4,6-difluoro-5-(4-methylpiperazin-1-yl)-1H-benzimidazol-2yl]-N-benzyloxy-acetamide (2.6 g, 4.64 mmol) is reacted with N,N'-carbonyldiimidazole (1.5 g, 9.28 mmol) in dimethylformamide (50 ml) at room temperature for 1 day. At the end of the reaction, the volatiles are evaporated under reduced pressure and the residue chromatographed on silica gel (eluent: 5% methanol-dichloromethane). The relevant fractions are concentrated in vacuo until crystals form. Filtration affords 0.57 g of 6-benzylamino-2-benzyloxy-5-cyclopropyl-7,9-difluoro-8-(4-methyl-piperazin-1-yl)-1,2,3,5-tetrahydro-pyrimido[1,6-a]benzimidazole-1,3-dione as colorless crystals (21%): mp: 214° C.; NMR (DMSO-$d_6$): 0.97 (m,2H),1.18(m,2H),2.23(s,3H),2.42(m,4H),3.13 (m,5H),4.35(d,J=6.5 Hz,2H),5.05(s,2H),5.36(s,1H),7.22–7.61 (m,11H).

Microanalysis: $C_{32}H_{32}F_2N_6O_3$: Calc: C:65.52, H:5.50, N:14.33%. Found: C:65.29, H:5.62, N:14.40%.

6-Benzylamino-2-benzyloxy-5-cyclopropyl-7,9-difluoro-8-(4-methylpiperazin-1-yl)-1,2,3,5-tetrahydro-pyrimido[1,6-a]benzimidazole-1,3-dione(0.57 g, 0.97 mmol), dissolved in ethanol (115 ml) and concentrated acetic acid (15 ml), is hydrogenated over 5% Pd/C (150 mg). At the end of the reaction, the catalyst is filtered off, and the solution is evaporated. The residue is dissolved in water (10 ml) and the pH adjusted to 7–8 with saturated aqueous sodium bicarbonate solution. The resulting crystals are collected by filtration, washed with water (10 ml) and dried, affording 0.32 g of 9-amino-5-cyclopropyl-6,8-difluoro-7-(4-methyl-1-piperazinyl)-2-hydroxy-pyrimido[1,6-a]benzimidazole-1,3-(2H, 5H)-dione as colorless crystals (80%): mp>250° C. (dec); NMR (DMSO-$d_6$): 0.97 (m,2H), 1.14 (m,2H), 2.22 (s,3H), 2.43 (m,4H), 3.13 (m,5H), 5.30 (s,1H), 6.25 (s,2H), 10.80 (broad, 1H).

Microanalysis: $C_{18}H_{20}F_2N_6O_3$: Calc: C:53.20, H:4.96, N:20.68%. Found: C:53.24, H:4.88, N:20.42%.

EXAMPLE A

Gelatin capsules containing the following ingredients are prepared in the usual manner:

| | |
|---|---|
| 5-Cyclopropyl-8-fluoro-7-(1--piperazinyl)-pyrimido[1,6-a]-benzimidazole-1,3(2H,5H)-dione | 200 mg |
| Luviskol (water-soluble polyvinylpyrrolidone) | 20 mg |
| Mannitol | 20 mg |
| Talc | 15 mg |
| Magnesium stearate | 2 mo |
| | 257 mg |

EXAMPLE B

Tablets containing the following ingredients are prepared in the usual manner:

| | |
|---|---|
| 5-Cyclopropyl-8-fluoro-7-(1--piperazinyl)-pyrimido[1,6-a]-benzimidazole-1,3-(2H,5H)-dione | 200 mg |
| Starch | 44 mg |
| Calcium carboxymethylcellulose | 30 mg |
| Crystalline cellulose | 40 mg |
| Magnesium stearate | 6 mg |
| | 320 mg |

We claim:
1. A compound of the formula

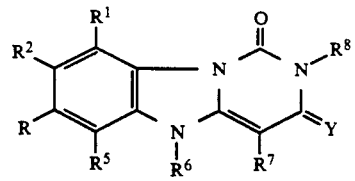

wherein
$R^1$ is hydrogen, halogen or amino,
$R^2$ is halogen,
R is a lower alkyl-substituted 4-pyridyl group or a group $R^3R^4N—$ in which $R^3$ and $R^4$ each are hydrogen or lower alkyl, or $R^3$ and $R^4$ together are a group of the formula $—(CH_2)_n—X—(CH_2)_m—$ or $—CH_2)_p—$ which is unsubstituted or substituted by lower alkyl, amino, lower aminoalkyl, mono- or di(lower alkyl)amino-lower alkyl, oxo or the group $—COOR^a$ or $—CONR'R''$,
n and m each are the number
p is the number 4, 5 or 6
X is the group $—NR'''—$,
$R^a$ is hydrogen, lower alkyl, lower alkenyl, phenyl or phenyl which is mono-, di- or trisubstituted by halogen, lower alkyl or hydroxy,
R' and R'' each are hydrogen or lower alkyl,
R''' is hydrogen, hydroxy, lower alkyl or lower aminoalkanoyl,
$R^5$ is hydrogen, halogen, lower alkoxy or amino,
$R^6$ is lower alkyl, lower cycloalkyl, lower haloalkyl, phenyl or phenyl which is mono-, di- or trisubstituted by halogen, lower alkyl, hydroxy or lower alkoxy,
$R^7$ is hydrogen, lower alkyl or carboxy,
$R^8$ is hydrogen, hydroxy, lower alkoxy, amino, lower alkylamino or di-lower alkylamino and
Y is an oxygen or sulfur atom,
or a pharmaceutically acceptable salt thereof.

2. A compound according to claim 1, wherein $R^8$ is hydrogen, hydroxy, lower alkoxy, amine or lower alkylamino.

3. A compound according to claim 2, wherein R is the group $R^3R^4N—$ and $R^8$ is hydrogen, hydroxy or lower alkoxy.

4. A compound according to claim 3, wherein $R^2$ is fluoro, R is a group $R^3R^4N—$, wherein $R^3R^4N$ is 1-piperazinyl or 4-methyl-1-piperazinyl, $R^6$ is ethyl or cyclopropyl, $R^7$ is hydrogen or carboxy, $R^8$ is hydrogen or hydroxy and Y is an oxygen atom.

5. A compound according to claim 3, wherein $R^1$ and $R^5$ each are hydrogen.

6. A compound according to claim 5, wherein $R^2$ is fluoro, R is a group $R^3R^4N—$, wherein $R^3R^4N$ is 1-piperazinyl or 4-methyl-1-piperazinyl, $R^6$ is ethyl or cyclopropyl, $R^7$ is hydrogen or carboxy, $R^8$ is hydrogen or hydroxy and Y is an oxygen atom.

7. A compound according to claim 5, wherein $R^2$ is fluorine.

8. A compound according to claim 7, wherein $R^3$ and $R^4$ together are a group of the formula $—(CH_2)_n—X—(CH_2)_m—$ or a group of the formula $—(CH_2)_p—$ which is substituted by the group $—COOR^a$, n and m each are the number 2, p is the number 4, X is the group —NR'''—, R$^a$ is lower alkyl and R''' is hydrogen, lower alkyl or lower aminoalkancyl.

9. A compound according to claim 8, wherein R$^3$R$^4$N— is the 1-piperazinyl group or the 4-methyl-1-piperazinyl group.

10. A compound according to claim 9, wherein R$^6$ is lower alkyl or lower cycloalkyl.

11. A compound according to claim 10, wherein R$^6$ is ethyl.

12. A compound according to claim 10, wherein R$^6$ is cyclopropyl.

13. A compound according to claim 12, wherein R$^7$ is hydrogen or carboxy.

14. A compound according to claim 13, wherein R$^8$ is hydrogen or hydroxy.

15. A compound according to claim 14, wherein Y is an oxygen atom.

16. A compound according to claim 2, wherein R is the 3,5-dimethyl-4-pyridyl group.

17. A compound according to claim 16, wherein R$^8$ is amino or methylamino.

18. A compound according to claim 16, wherein R$^8$ is dimethylamino.

19. The compound according to claim 1, 5-ethyl-6-fluoro-7-(4-methyl-1-piperazinyl)-pyrimido[1,6-a]-benzimidazole-1,3(2H,5H)-dione.

20. The compound according to claim 1, 5-cyclopropyl-8-fluoro-7-(1-piperazinyl)-pyrimido[1,6-a]benzimidazole-1,3(2H,5H)-dione or a salt thereof.

21. The compound according to claim 1, 5-ethyl-9-fluoro-3,5-dihydro-8-(4-methyl-1-piperazinyl)-3-thioxopyrimido[1,6-a]benzimidazol-1(2H)-one.

22. The compound according to claim 1, 5-cyclopropyl-8-fluoro-2-hydroxy-7-(1-piperazinyl)pyrimido[1,6-a]-benzimidazole-1,3(2H, 5H)-dione.

23. The compound according to claim 1, 7-(4-L-alanyl-1-piperazinyl)-5-cyclopropyl-8-fluoro-2-hydroxypyrimido-[1,6-a]benzimidazole-1,3(2H, 5H)-dione.

24. The compound according to claim 1, 1-[5-cyclopropyl-8-fluoro-1,2,3,5-tetrahydro-2-hydroxy-1,3-dioxopyrimido[1,6-a]benzimidazol-7-yl]-L-proline tert-butyl ester.

25. The compound according to claim 1, 5-ethyl-8-fluoro-7-(1-piperazinyl)pyrimido[1,6-a]benzimidazole-1,3(2H, 5H)-dione.

26. The compound according to claim 1, 5-ethyl-8-fluoro-2-hydroxy-7-(4-methyl-1-piperazinyl)-pyrimido[1,6-a]benzimidazole-1,3(2H, 5H)-dione.

27. The compound according to claim 1, 5-cyclopropyl-8-fluoro-1,2,3,4-tetrahydro-1,3-dioxo-7-(1-piperazinyl)pyrimido[1,6-a]benzimidazole-4-carboxylic acid.

28. The compound according to claim 1, 5-ethyl-8-fluoro-2-hydroxy-7-(1-piperazinyl)pyrimido[1,6-a]-benzimidazole-1,3(2H, 5H)-dione or a salt thereof.

29. The compound according to claim 1, 2-amino-5-cyclopropyl-8-fluoro-7-(1-piperazinyl)pyrimido[1,6-a]benzimidazole-1,3(2H, 5H)-dione.

30. The compound according to claim 1, 5-cyclopropyl-8-fluoro-2-(methylamino)-7-(1-piperazinyl)-pyrimido[1,6-a]benzimidazole-1,3(2H, 5H)-dione.

31. The compound according to claim 1, 5-cyclopropyl-2-(dimethylamino)-8-fluoro-7-(1-piperazinyl)-pyrimido[1,6-a]benzimidazole-1,3(2H,5H)-dione.

32. A compound according to claim 1, wherein R$^1$, R$^5$ and R$^7$ are hydrogen, R is 4-methyl-1-piperazinyl, R$^6$ is cyclopropyl, R$^8$ is hydroxy and Y is oxygen.

33. A compound according to claim 32, 5-cyclopropyl-8-fluoro-2-hydroxy-7-(4-methyl-1-piperazinyl)-1H-pyrimido[1,6-a]benzimidazole-1,3(2H, 5H)-dione.

34. The compound according to claim 1, tert-butyl rac-1-[5-cyclopropyl-8-fluoro-2,3-dihydro-1,3dioxopyrimido[1,6-a]benzimidazol-7-(1H)-yl]-2-pyrrolidinecarboxylate.

35. A pharmaceutical composition comprising an effective amount of a compound of the formula

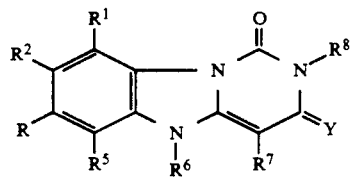

wherein
R$^1$ is hydrogen, halogen or amino,
R$^2$ is halogen,
R is a lower alkyl-substituted 4-pyridyl group or a group R$^3$R$^4$N— in which R$^3$ and R$^4$ each are hydrogen or lower alkyl, or R$^3$ and R$^4$ together are a group of the formula —(CH$_2$)$_n$—X—(CH$_2$)$_m$— or —(CH$_2$)$_p$— which is unsubstituted or substituted by lower alkyl, amino, lower aminoalkyl, mono- or di(lower alkyl)amino-lower alkyl, oxo or the group —COOR$^a$ or —CONR'R'',
n and m each are the number 2
p is the number 4, 5 or 6,
X is the group —NR'''—,
R$^a$ is hydrogen, lower alkyl, lower alkenyl, phenyl or phenyl which is mono-, di- or trisubstituted by halogen, lower alkyl or hydroxy,
R' and R'' each are hydrogen or lower alkyl,
R''' is hydrogen, hydroxy, lower alkyl or lower aminoalkanoyl,
R$^5$ is hydrogen, halogen, lower alkoxy or amino,
R$^6$ is lower alkyl, lower cycloalkyl, lower haloalkyl, phenyl or phenyl which is mono-, di- or trisubstituted by halogen, lower alkyl, hydroxy or lower alkoxy,
R$^7$ is hydrogen, lower alkyl or carboxy,
R$^8$ is hydrogen, hydroxy, lower alkoxy, amino, lower alkylamino or di-lower alkylamino and,
Y is an oxygen or sulfur atom,
and a therapeutically inert carrier.

36. A pharmaceutical composition in accordance with claim 35, wherein R$^8$ is hydrogen, hydroxy, lower alkoxy, amino or lower alkylamino.

37. A pharmaceutical composition in accordance with claim 36, wherein R is the group R$^3$R$^4$N— and R$^8$ is hydrogen, hydroxy or lower alkoxy.

38. A pharmaceutical composition in accordance with claim 37, wherein R$^1$ and R$^5$ each are hydrogen.

39. A pharmaceutical composition in accordance with claim 38, wherein R$^2$ is fluorine.

40. A pharmaceutical composition in accordance with claim 39, wherein R$^3$ and R$^4$ together are a group of the formula —(CH$_2$)$_n$—X—(CH$_2$)$_m$— or a group of the formula —(CH$_2$)$_p$— which is substituted by the group —COOR$^a$, n and m each are the number 2, p is the number 4, X is the group —NR'''—, R$^a$ is lower alkyl and R''' is hydrogen, lower alkyl or lower aminoalkanoyl.

41. A pharmaceutical composition in accordance with claim 40, wherein R³R⁴N— is the 1-piperazinyl group or the 4-methyl-1-piperazinyl group.

42. A pharmaceutical composition in accordance with claim 41, wherein R⁶ is lower alkyl or lower cycloalkyl.

43. A pharmaceutical composition in accordance with claim 42, wherein R⁶ is ethyl.

44. A pharmaceutical composition in accordance with claim 42, wherein R⁶ is cyclopropyl.

45. A pharmaceutical composition in accordance with claim 44, wherein R⁷ is hydrogen or carboxy.

46. A pharmaceutical composition in accordance with claim 45, wherein R⁸ is hydrogen or hydroxy.

47. A pharmaceutical composition in accordance with claim 46, wherein Y is an oxygen atom.

48. A pharmaceutical composition in accordance with claim 36, wherein R is the 3,5-dimethyl-4-pyridyl group.

49. A pharmaceutical composition in accordance with claim 35, wherein R is the 3,5-dimethyl-4-pyridyl group.

50. A pharmaceutical composition in accordance with claim 48, wherein R⁸ is amino or methylamino.

51. A pharmaceutical composition in accordance with claim 48, wherein R⁸ is dimethylamino.

52. A pharmaceutical composition according to claim 35, wherein R¹, R⁵ and R⁷ are hydrogen, R is 4-methyl-1-piperazinyl, R⁶ is cyclopropyl, R⁸ is hydroxy and Y is oxygen.

53. A method of preventing or treating a bacterial infectious disease which comprises administering to a warm blooded animal an effective amount of a compound of the formula

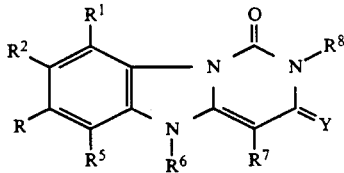

wherein
R¹ is hydrogen, halogen or amino,
R² is halogen,
R is a lower alkyl-substituted 4-pyridyl group or a group R³R⁴N— in which R³ and R⁴ each are hydrogen or lower alkyl, or R³ and R⁴ together signify a group of the formula —(CH₂)ₙ—X—(CH₂)ₘ— or —(CH₂)ₚ— which is unsubstituted or substituted by lower alkyl, amino, lower aminoalkyl, mono- or di(lower alkyl)-amino-lower alkyl, oxo or the group —COORᵃ or —CONR'R",
n and m each are the number 2,
p is the number 4, 5 or 6,
X is the group —NR'''—, Rᵃ is hydrogen, lower alkyl, lower alkenyl, phenyl or phenyl which is mono-, di- or trisubstituted by halogen, lower alkyl or hydroxy,
R' and R" each are hydrogen or lower alkyl,
R''' is hydrogen, hydroxy, lower alkyl or lower aminoalkanoyl,
R⁵ is hydrogen, halogen, lower alkoxy or amino,
R⁶ is lower alkyl, lower cycloalkyl, lower haloalkyl, phenyl or phenyl which is mono-, di- or trisubstituted by halogen, lower alkyl, hydroxy or lower alkoxy,
R⁷ is hydrogen, lower alkyl or carboxy,
R⁸ is hydrogen, hydroxy, lower alkoxy, amino, lower alkylamino or di-lower alkylamino and,
Y is an oxygen or sulfur atom.

54. A method according to claim 53, wherein R⁸ is hydrogen, hydroxy, lower alkoxy, amino or lower alkylamino.

55. A method according to claim 54, wherein R is the group R³R⁴N— and R⁸ is hydrogen, hydroxy or lower alkoxy.

56. A method according to claim 55, wherein R¹ and R⁵ each are hydrogen.

57. A method according to claim 56, wherein R² is fluorine.

58. A method according to claim 57, wherein R³ and R⁴ together are a group of the formula —(CH₂)ₙ—X—(CH₂)ₘ— or a group of the formula —(CH₂)ₚ— which is substituted by the group —COORᵃ, n and m each are the number 2, p is the number 4, X is the group —NR'''—, Rᵃ is lower alkyl and R''' is hydrogen, lower alkyl or lower aminoalkanoyl.

59. A method according to claim 58, wherein R³R⁴N— is the 1-piperazinyl group or the 4-methyl-1-piperazinyl group.

60. A method according to claim 59, wherein R⁶ is lower alkyl or lower cycloalkyl.

61. A method according to claim 60, wherein R⁶ is ethyl.

62. A method according to claim 60, wherein R⁶ is cyclopropyl.

63. A method according to claim 62, wherein R⁷ is hydrogen or carboxy.

64. A method according to claim 63, wherein R⁸ is hydrogen or hydroxy.

65. A method according to claim 64, wherein Y is an oxygen atom.

66. A method according to claim 54, wherein R is the 3,5-dimethyl-4-pyridyl group.

67. A method according to claim 53, wherein R is the 3,5-dimethyl-4-pyridyl group.

68. A method according to claim 66, wherein R⁸ is amino or methylamino.

69. A method according to claim 66, wherein R⁸ is dimethylamino.

70. A method according to claim 53, wherein R¹, R⁵ and R⁷ are hydrogen, R is 4-methyl-1-piperazinyl, R⁶ is cyclopropyl, R⁸ is hydroxy and Y is oxygen.

* * * * *